(12) United States Patent
Bugni et al.

(10) Patent No.: US 10,889,551 B2
(45) Date of Patent: Jan. 12, 2021

(54) BIEMAMIDES AND RELATED SCAFFOLDS AS INHIBITORS OF TRANSFORMING GROWTH FACTOR-BETA SIGNALING

(71) Applicant: Wisconsin Alumni Research Foundation, Madison, WI (US)

(72) Inventors: Timothy Bugni, Madison, WI (US); Fan Zhang, Madison, WI (US); Douglas Braun, Mount Horeb, WI (US); Gene Ananiev, Middleton, WI (US); F. Michael Hoffmann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/551,534

(22) Filed: Aug. 26, 2019

(65) Prior Publication Data
US 2020/0062715 A1 Feb. 27, 2020

Related U.S. Application Data

(60) Provisional application No. 62/723,416, filed on Aug. 27, 2018.

(51) Int. Cl.
*C07D 239/22* (2006.01)
(52) U.S. Cl.
CPC .................. *C07D 239/22* (2013.01)
(58) Field of Classification Search
CPC .................................................. C07D 239/22
See application file for complete search history.

(56) References Cited

FOREIGN PATENT DOCUMENTS

JP 2017214304 A 12/2017

OTHER PUBLICATIONS

Zhang, et al., Biemamides A-E, Inhibitors of the TGF-β Pathway That Block the Epithelial to Mesenchymal Transition, Org. Lett., 20, 18, 5529-5532 (2018) (Year: 2018).*
Ji et al., "Rho/Rock cross talks with transforming growth factor β/Smad pathway participates in lung fibroblast myofibroblast differentiation", Biomedical Reports 2: 787-792 (2014).
Marfey, Peter, "Determination of o-Amino Acids. II. Use of a Bifunctional Reagent, 1, 5-Difluoro-2,4-Dinitrobenzene" Carlsberg Res. Commun. vol. 49, p. 591-596, (1984).
Padgett et al., "TGF-b signaling, Smads, and tumor suppressors", BioEssays 20:382-391, (1998).
Pan et al., "Identification and Characterization of the Antifungal Substances of a Novel *Streptomyces cavourensis* NA4", J. Microbiol. Biotechnol. (2015), 25(3), 353-357.
Reasoner et al., "A New Medium for the Enumeration and Subculture of Bacteria from Potable Water", Applied and Environmental Microbiology, Jan. 1985, p. 1-7, vol. 49, No. 1.
Savage-Dunn, C., "TGF-signaling" (Sep. 9, 2005), WormBook, ed. The C. elegans Research Community, WormBook, doi/10.1895/wormbook.I.22. I, http://www.wormbook.org.
Shirling et al., "Methods for Characterization of *Streptomyces* Species", Int. J Syst. Bacterial, 16, 313-340 (1966).

* cited by examiner

*Primary Examiner* — Erich A Leeser
(74) *Attorney, Agent, or Firm* — Foley & Lardner LLP (57) ABSTRACT

The present technology provides an isolated compound of Formula I, compositions including such compounds, methods of inhibiting TGF-β signaling and/or TGF-β induced epithelial mesenchymal transitions (EMT), and treating certain cancers involving TGF-β signaling and/or EMT.

9 Claims, 5 Drawing Sheets

BIEMAMIDES AND RELATED SCAFFOLDS AS INHIBITORS OF TRANSFORMING GROWTH FACTOR-BETA SIGNALING

CROSS-REFERENCE TO RELATED PATENT APPLICATIONS

The present application claims priority to U.S. provisional application No. 62/723,416, filed Aug. 27, 2018, the contents of which is hereby incorporated by reference herein in its entirety.

STATEMENT OF GOVERNMENT SUPPORT

This invention was made with government support under GM104192 awarded by the National Institutes of Health. The government has certain rights in the invention.

FIELD

The present technology relates generally to a new class of compounds called biemamides, compositions thereof, and methods of use thereof. Specifically, the new isolated compounds are useful in inhibiting transforming growth factor-beta (TGF-β) signaling and TGF-β-induced epithelial mesenchymal transitions (EMT).

BACKGROUND

TGF-β regulates many biological processes. In particular, TGF-β plays prominent roles in human disease; for example, TGF-β is a central player in tumor growth, invasion and subsequent metastasis. Epithelial to mesenchymal transitions (EMTs) are paramount to a variety of developmental processes and are largely mediated by TGF-β. Significantly, EMT dictates, to a large degree, the lethality of human cancers; primary tumor cells that have undergone EMT pose a tremendous threat by virtue of their capacity to trigger tumor metastasis. TGF-β also coordinately upregulates the expression of many matrix proteins, and has been shown to play a causative role in the progression of many fibrotic disorders. For example, aberrant EMTs are a critical feature of end-stage organ failure by fibrosis. Accordingly, new TGF-β inhibitors could serve as useful biochemical tools as well as prospective therapeutics for fibrotic and oncological diseases. The present technology relates to compounds and compositions and their use in methods of treatment of diseases or disorders mediated by TGF-β and inhibition of TGF-β signaling and EMT.

SUMMARY

In an aspect, the present technology provides compounds, including isolated compounds, of Formula I:

(I)

a stereoisomer, a tautomer, and/or a pharmaceutically acceptable salt thereof, wherein:

$R^1$ is a $C_{12}$-$C_{18}$ alkyl or alkenyl;
$R^2$ is a $C_1$-$C_6$ alkyl; and
n is 1, 2, 3, 4, 5, or 6;
provided that when n is 2 and $R^2$ is methyl, $R^1$ is not a $C_{15}$ or $C_{16}$ alkyl.

In a related aspect, the present technology provides pharmaceutical compositions for inhibiting TGF-β signaling including an effective amount of any of the isolated or synthesized compounds described herein in any embodiment, a stereoisomer, a tautomer, and/or a pharmaceutically acceptable salt thereof, and a pharmaceutically acceptable carrier.

In another aspect, the present technology provides a method of treatment that includes administering to a mammal suffering from a disease or disorder mediated by TGF-β signaling, an effective amount of a compound described herein in any embodiment, a stereoisomer, tautomer, or pharmaceutically acceptable salt thereof, or a pharmaceutical composition comprising the effective amount of the compounds described herein in any embodiment, stereoisomer, tautomer, or pharmaceutically acceptable salt thereof, and a pharmaceutically acceptable carrier.

In yet another aspect, the present technology provides a method of inhibiting TGF-β signaling comprising contacting a TGF-β signaling system with an effective amount of a compound of Formula I:

(I)

a stereoisomer, a tautomer, and/or a pharmaceutically acceptable salt thereof;
wherein:
$R^1$ is a $C_{12}$-$C_{18}$ alkyl or alkenyl;
$R^2$ is a $C_1$-$C_6$ alkyl; and
n is 1, 2, 3, 4, 5, or 6;
or a pharmaceutical composition comprising the effective amount of the compound of Formula I, stereoisomer, tautomer, and/or pharmaceutically acceptable salt thereof, and a pharmaceutically acceptable carrier, wherein the effective amount inhibits TGF-β signaling.

BRIEF DESCRIPTION OF THE DRAWINGS

FIGS. 3A-3D shows the morphology of treated and untreated NMuMG epithelial cells.

FIG. 3A shows the morphology of untreated NMuMG epithelial cells. FIG. 3B shows NMuMG cells treated with 50 pM TGF-β. FIG. 3C shows 50 pM TGF-β treated NMuMG epithelial cells, subsequently incubated with 160 nM compound 1 (biemamide A) for 72 h. FIG. 3D shows 50 pM TGF-β treated NMuMG epithelial cells incubated with 1 µM SB431542 (positive control) for 72 h.

FIGS. 5A-5E shows phenotypes of *C. elegans* treated with compound 1 (200 m scale). FIG. 5A shows *C. elegans* with no treatment. FIG. 5B shows *C. elegans* treated with 10 µM of compound 1. FIG. 5C shows *C. elegans* treated with 1 µM of compound 1. FIG. 5D shows *C. elegans* treated with 100 nM of compound 1. FIG. 5E shows *C. elegans* treated with 10 nM of compound 1.

DETAILED DESCRIPTION

In various aspects, the present technology provides isolated or synthesized compounds, and methods using such compounds for the inhibition of TGF-β signaling and epithelial mesenchymal transitions (EMT), as well as the treatment of diseases and disorders mediated by TGF-β signaling and EMTs. The isolated or synthesized compounds provided herein can be formulated into pharmaceutical compositions and medicaments that are useful in the disclosed methods. Also provided is the use of the isolated or synthesized compounds in preparing pharmaceutical formulations and medicaments.

The following terms are used throughout as defined below.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Alkyl groups include straight chain and branched chain alkyl groups having from 1 to 20 carbon atoms, and typically from 1 to 18 carbons or, in some embodiments, from 1 to 15, 1 to 12, 1 to 10, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups.

Alkenyl groups include straight and branched chain alkyl groups as defined above, except that at least one double bond exists between two carbon atoms. Alkenyl groups have from 2 to 20 carbon atoms, and typically from 2 to 18 carbons or, in some embodiments, from 2 to 15, 2 to 12, 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi— and tricyclic ring systems include both bridged cycloalkyl groups and fused rings, such as, but not limited to, bicyclo[2.1.1] hexane, adamantyl, decalinyl, and the like.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

As another example, guanidines may exhibit the following isomeric forms in protic organic solution, also referred to as tautomers of each other:

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In one aspect, the present technology provides isolated or synthesized compounds that inhibit TGF-β signaling and epithelial mesenchymal transitions (EMT). Thus, the present technology includes an isolated compound of Formula I:

a stereoisomer, a tautomer, and/or a pharmaceutically acceptable salt thereof, wherein:

$R^1$ is a $C_{12}$-$C_{18}$ alkyl or alkenyl;

$R^2$ is a $C_1$-$C_6$ alkyl; and n is 1, 2, 3, 4, 5, or 6;

provided that when n is 2 and $R^2$ is methyl, $R^1$ is not a $C_{15}$ or $C_{16}$ alkyl.

In any embodiment of the isolated compounds of Formula I, $R^1$ may be a $C_{12}$-$C_{18}$ alkyl or alkenyl, a $C_{15}$-$C_{18}$ alkyl or alkenyl, or a $C_{15}$-$C_{17}$ alkyl or alkenyl. For example, in any embodiment herein, $R^1$ may be a $C_{15}$-$C_{17}$ alkyl or alkenyl. Thus, in any embodiment herein, $R^1$ may be

In any embodiment herein, $R^2$ may be a methyl, ethyl, propyl, butyl, pentyl, or hexyl. Thus, in any embodiment herein, $R^2$ may be a methyl. In any embodiment of an isolated compound of Formula I, n may be 1, 2, 3, 4, 5, or 6. For example, in any embodiment herein, n may be 2.

The isolated compound may be a compound of Formula IA:

(IA)

a tautomer and/or a pharmaceutically acceptable salt thereof, wherein: $R^1$ is a $C_{15}$-$C_{17}$ alkyl or alkenyl. For example, in any embodiment herein, the compound of Formula IA may include, but is not limited to, a compound of Formulae IIA, IIB, IIC, IID, or IIE,

(IIA)

(IIB)

(IIC)

(IID), and (IIE)

tautomers thereof and/or pharmaceutically acceptable salts thereof.

The isolated compounds described herein in any embodiment may be isolated at various purities, e.g., a purity of at least 60 wt %, at least 70 wt %, at least 80 wt %, at least 90 wt %, at least 95 wt %, at least 96 wt %, at least 97 wt %, at least 98 wt %, at least 99 wt %, or at least 99.5 wt %.

In a related aspect, the present technology provides a pharmaceutical composition for inhibiting TGF-β signaling including an effective amount of any of the isolated compounds described herein in any embodiment, a stereoisomer, a tautomer, and/or a pharmaceutically acceptable salt thereof, and a pharmaceutically acceptable carrier. The pharmaceutical compositions may be used in the methods and treatments described herein. The pharmaceutical composition may include an effective amount of any one of the embodiments of the isolated or synthesized compounds of the present technology disclosed herein. In any of the above embodiments, the effective amount may be determined in relation to a subject. "Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the inhibition of TGF-β signaling and EMT. Another example of an effective amount includes amounts or dosages that yield acceptable toxicity and bioavailability levels for therapeutic (pharmaceutical) use including, but not limited to, treatment of TGF-β mediated diseases or disorders (such as liver fibrosis, lung fibrosis, kidney fibrosis, skin fibrosis, myelofibrosis, hepatocellular carcinoma, and non-small cell lung cancer). As used herein, a "subject" or "patient" is a mammal, such as a cat, dog, rodent or primate. Typically, the subject is a human, and, preferably, a human suffering from a disease or disorder mediated by TGF-β. The term "subject" and "patient" can be used interchangeably.

Thus, pharmaceutical compositions of the present technology may include any compound of Formula I described herein (including but not limited to a compound of any of Formulae IA, IIA-IIE) a stereoisomer, a tautomer, and/or a pharmaceutically acceptable salt thereof, and a pharmaceutically acceptable carrier.

Pharmaceutical compositions of the present technology may further include one or more excipients, binders, diluents, additives, or the like, or combinations of two or more thereof. The compounds and compositions described herein may be used to prepare formulations and medicaments that inhibit TGF-β signaling or treat a variety of diseases or disorders associated with or mediated by TGF-β signaling, as described herein. Such compositions may be in the form of, for example, granules, powders tablets, capsules, syrup, suppositories, injections, emulsions, elixirs, suspensions, or solutions. The pharmaceutical compositions may be formulated for various routes of administration. For example, the pharmaceutical compositions and medicaments in any embodiment herein may be formulated for oral, parenteral, nasal, or topical administration. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or stereoisomers, tautomers, and/or pharmaceutically acceptable salts thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration may include as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until for example, the desired therapeutic response is observed. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including age, protocol, condition, sex, severity/extent of disease/disorder being treated, contraindications, the pharmacological activity of the compound being used, concomitant therapies and the like. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease TGF-β signaling, such as, for example, a decrease in or inhibition of EMT. Effectiveness of the compositions and methods of the present technology may also be demonstrated by a decrease in or prevention of tumor growth, invasion, and subsequent metastasis of hepatocellular carcinoma or non-small cell lung cancer, or decrease fibrogenic stimuli leading to fibrotic diseases (such as myelofibrosis liver fibrosis, lung fibrosis, kidney fibrosis, and skin fibrosis)

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In another aspect, the present technology provides a method of treatment that includes administering to a mammal suffering from a disease or disorder mediated by TGF-β signaling, an effective amount of a compound of Formula I as described herein in any embodiment (including but not limited to a compound of Formula IA, IIA, IIB, IIC, IID, or IIE), a stereoisomer, tautomer, or pharmaceutically acceptable salt thereof, or a pharmaceutical composition comprising the effective amount of the compound of Formula I (including but not limited to a compound of Formula IA, IIA, IIB, IIC, IID, or IIE), stereoisomer, tautomer, or pharmaceutically acceptable salt thereof, and a pharmaceutically acceptable carrier.

The mammal may be, e.g., a human, primate (e.g., monkey, chimpanzee, ape), cat, dog, pig, mouse, rat, horse, sheep, among others. In any embodiment described herein, the mammal may be human. The TGF-β mediated disease or disorder may be hepatocellular carcinoma, non-small cell lung cancer, liver fibrosis, lung fibrosis, kidney fibrosis, skin fibrosis, or myelofibrosis. In any embodiment herein, the method of treatment may decrease or inhibit TGF-β mediated tumor growth, invasion, or metastasis in a subject suffering from hepatocellular carcinoma or non-small cell lung cancer. In any embodiment herein, the method of treatment may decrease or inhibit In another related aspect, the present technology provides a method of inhibiting TGF-β signaling comprising contacting a TGF-β signaling system with an effective amount of any compound of Formula I described herein, (including but not limited to compounds of Formula IA, and IIA-IIE) a tautomer and/or pharmaceutically acceptable salt thereof, or a pharmaceutical composition that includes an effective amount of a compound of Formula I, a tautomer and/or pharmaceutically acceptable salt thereof, and a pharmaceutically acceptable carrier.

In any embodiment herein, the method of inhibiting TGF-β signaling may include inhibiting TGF-β signaling at concentrations of any of the compounds described herein, stereoisomers, tautomers, and/or pharmaceutically acceptable salts thereof, of about 0.5 nM to about 100 μM. Suitable concentrations in any embodiment herein may include, but are not limited to about 0.5 nM, about 1 nM, about 2 nM, about 3 nM, about 4 nM, about 5 nM, about 6 nM, about 7 nM, about 8 nM, about 9 nM, about 10 nM, about 15 nM, about 20 nM, about 30 nM, about 40 nM, about 50 nM, about 60 nM, about 70 nM, about 80 nM, about 90 nM, about 100 nM, about 150 nM, about 200 nM about 300 nM, about 400 nM, about 500 nM, about 600 nM, about 700 nM, about 800 nM, about 900 nM, about 1 μM, about 5 μM, about 10 μM, about 20 μM, about 40 μM, about 60 μM, about 80 μM, about 100 μM, or any range including and/or in between any two the preceding values. For example, in any embodiment herein, the concentration may include from about 0.5 nM to about 50 μM, about 0.5 nM to about 10 μM, about 0.5 nM to about 1 j, about 0.5 nM to about 500 nM, or about 0.5 nM to about 100 nM. The effective amount includes an amount effective to inhibit TGF-β induced EMT.

The present invention, thus generally described, will be understood more readily by reference to the following examples, which are provided by way of illustration and are not intended to be limiting of the present invention.

EXAMPLES

General Experimental Procedures

Optical rotations were measured on a PerkinElmer 241 polarimeter. UV spectra were recorded on an Aminco/OLIS UV-Vis spectrophotometer. IR spectra were measured with a Bruker Equinox 55/S FT-IR spectrophotometer. ECD spectra were recorded on an AVIV Model 420 Circular Dichroism Spectrometer. NMR spectra were obtained in DMSO-$d_6$ with a Bruker Avance 500 MHz spectrometer equipped with a $^1H\{^{13}C/^{15}N\}$ cryoprobe and a Bruker Avance 500 MHz spectrometer equipped with a $^{13}C/^{15}N\{^1H\}$ cryoprobe. HRMS data were acquired with a Bruker MaXis 4G QTOF mass spectrometer.

Example 1: Isolation of Biemamides from Bacteria Associated with Ascidiacea

Biological Material. Ascidians specimens were collected in September 2011 from the Florida Keys (24°33.416', 81°21.611'). A voucher specimen for *Ecteinascidia turbinata* (Herdman, 1880) is housed at the University of Wisconsin-Madison. For cultivation, a sample of ascidian (1 cm$^3$) was rinsed with sterile seawater, macerated using a sterile pestle in a micro-centrifuge tube, and dilutions were made in sterile seawater, with vortexing between steps to separate bacteria from heavier tissues. Dilutions were separately plated on four media: ISP2, R2A, ISP3, and Gauze 1 as previously reported (Shirling, E. B.; Gottlieb, D. Int. *J. Syst. Bacteriol.* 1966, 16, 313-340; Reasoner, D. J.; Geldreich, E. E. Appl. Environ. Microbiol. 1985, 49, 1-7; Pan H.; Yu, S.; Song, C.; Wang, N.; Hua, H.; Hu, J.; Wang, S. *J. Microbiol. Biotechnol.* 2015, 25, 353-357). Each medium was supplemented with 50 μg/mL cycloheximide and 25 μg/mL nalidixic acid. Plates were incubated at 28° C. for at least 28 days, and strain WMMA 2266 was purified from a Gauze 1 isolation plate.

Sequencing.

Genomic DNA was extracted using the UltraClean Microbial DNA Isolation kit (Mo Bio Laboratories, Inc.). 16S rDNA genes were amplified using 100-200 ng genomic DNA template with the primers 8-27F (5' to 3' GAGTTT-GATCCTGGCTCAG) and 1492R (5' to 3' GGT-TACCTTGTTACGACTT). The following PCR conditions were used: 94° C. for 5 min, followed by 30 cycles of 94° C. for 30 s, 55° C. for 1 min, 72° C. for 1.5 min, with a final step of 72° C. for 5 min. The PCR bands were excised from the gel and purified using the QIAquick Gel Extraction kit (QIAGEN). One μL purified product was sequenced. Sequencing reactions were performed by the UW Biotechnology Center and reactions were sequenced with an ABI 3730xl DNA Analyzer. WMMA 2266 were identified as *Streptomyces* sp. by 16S sequencing, and accession number was MH231155.

Fermentation, Extraction, and Isolation. Two 10 mL seed cultures (25×150 mm tubes) in medium ASW-A (20 g soluble starch, 10 g glucose, 5 g peptone, 5 g yeast extract, 5 g CaCO$_3$ per liter of artificial seawater) were inoculated with strain WMMA 2266 and shaken (200 RPM, 28° C.) for seven days. Two-liter flasks (2×500 mL) containing Ram2 medium (4 g corn meal, 10 g glucose, 15 g maltose, 7.5 g pharmamedia, 5 g yeast per liter of 50% artificial seawater) with Diaion HP20 (7% by weight) were inoculated with 10 mL of seed culture and shaken at 200 rpm at 28° C. for seven days. Filtered HP20 was washed with water and extracted with acetone. The acetone extract (10 g) was subjected to liquid-liquid partitioning using 30% aqueous CH$_3$OH and CHCl$_3$ (1:1). The CHCl$_3$-soluble partition (3.5 g) was subjected to ENV$^+$ column chromatography with H$_2$O and CH$_3$OH (25%, 50%, 75% and 100%). The 100% CH$_3$OH fraction was subjected to RP HPLC (10%/90% CH$_3$CN/H$_2$O with H$_2$O containing 0.1% acetic acid for 2 min, followed by 10%/90% to 30%/70% CH$_3$CN/H$_2$O for 3 min, then followed by 30%/70% to 100%/0% CH$_3$CN/H$_2$O over 14 min, and a hold at 100%/0% of CH$_3$CN for 13 min, 20 mL/min) using a Phenomenex Onyx Monolithic C$_{18}$ column (100×10 mm). The fraction containing Compound 1 and Compound 2 was further subjected to RP HPLC (85%/15% CH$_3$CN/H$_2$O with H$_2$O containing 0.1% acetic acid over 30 min, 4 mL/min) using a Phenomenex Luna C$_{18}$ column (250×10 mm, 5 μm), yielding Compound 1 (6.0 mg, $t_R$ 24.8 min) and Compound 2 (1.6 mg, $t_R$ 26.5 min). The fraction containing Compound 3 and Compound 4 was further subjected to RP HPLC (50%/50% to 70%/30% CH$_3$CN/H$_2$O with H$_2$O containing 0.1% acetic acid over 35 min, 4 mL/min) using a Phenomenex Luna C$_{18}$ column (250×10 mm, 5 μm), yielding Compound 3 (2.0 mg, $t_R$ 25.7 min) and Compound 4 (1.8 mg, $t_R$ 26.9 min). The fraction containing Compound 5 was further subjected to RP HPLC (50%/50% to 65%/35% CH$_3$CN/H$_2$O with H$_2$O containing 0.1% acetic acid over 50 min, 4 mL/min) using a Phenomenex Luna C$_{18}$ column (250×10 mm, 5 μm), yielding Compound 5 (2.0 mg, $t_R$ 39.7 min).

| Compound No. | Structure |
|---|---|
| 1 | (Biemamide A) |
| 2 | (Biemamide B) |
| 3 | (Biemamide C) |
| 4 | (Biemamide D) |
| 5 | (Biemamide E) |

Example 2: Structure Elucidation

Analytical data were gathered for Biemamides A-E, including optical rotation, IR, HRMS, and NMR spectra.

Biemamide A (1): white powder; $[\alpha]^{25}_D$-40 (c 0.1, CH$_3$OH/CHCl$_3$ 1:1); UV (CH$_3$OH/CHCl$_3$ 1:1) $\lambda_{max}$ (log ε) 237 (2.75) nm; IR (ATR) $\upsilon_{max}$ 3305, 2918, 2851, 1754, 1671, 1642, 1577, 1419, 1327, 1272, 1079, 1044, 1013, 668 cm$^{-1}$; $^1$H and $^{13}$C NMR (Table 1); HRESIMS [M+Na]$^+$ m/z 475.3250 (calcd for C$_{24}$H$_{44}$N$_4$O$_4$Na$^+$, 475.3255).

Biemamide B (2): white powder; $[\alpha]^{25}_D$-38 (c 0.05, CH$_3$OH/CHCl$_3$ 1:1); UV (CH$_3$OH/CHCl$_3$ 1:1) $\lambda_{max}$ (log ε) 236 (2.74) nm; IR (ATR) $\upsilon_{max}$ 3302, 2922, 2852, 1755, 1670, 1642, 1578, 1418, 1326, 1273, 1079, 1044, 1013, 668 cm$^{-1}$; $^1$H and $^{13}$C NMR (Table 2); HRESIMS [M+Na]$^+$ m/z 475.3246 (calcd for C$_{24}$H$_{44}$N$_4$O$_4$Na$^+$, 475.3255).

Biemamide C (3): white powder; $[\alpha]^{25}_D$-50 (c 0.03, CH$_3$OH/CHCl$_3$ 1:1); UV (CH$_3$OH/CHCl$_3$ 1:1) $\lambda_{max}$ (log ε) 238 (2.73) nm; IR (ATR) $\upsilon_{max}$ 3302, 2924, 2853, 1753, 1734, 1717, 1699, 1642, 1578, 1419, 1327, 1275, 1034, 758 cm$^{-1}$; $^1$H and $^{13}$C NMR (Table 3); HRESIMS [M+Na]$^+$ m/z 473.3085 (calcd for C$_{24}$H$_{42}$N$_4$O$_4$Na$^+$, 473.3098).

Biemamide D (4): white powder; $[\alpha]^{25}_D$-43 (c 0.04, CH$_3$OH/CHCl$_3$ 1:1); UV (CH$_3$OH/CHCl$_3$ 1:1) $\lambda_{max}$ (log ε) 237 (2.74) nm; IR (ATR) $\upsilon_{max}$ 3304, 2925, 2854, 1755, 1733, 1717, 1699, 1642, 1578, 1419, 1327, 1275, 1034, 758 cm$^{-1}$; $^1$H and $^{13}$C NMR (Table 4); HRESIMS [M+Na]$^+$ m/z 473.3086 (calcd for C$_{24}$H$_{42}$N$_4$O$_4$Na$^+$, 473.3098).

Biemamide E (5): white powder; $[\alpha]^{25}_D$-37 (c 0.05, CH$_3$OH/CHCl$_3$ 1:1); UV (CH$_3$OH/CHCl$_3$ 1:1) $\lambda_{max}$ (log ε) 237 (2.76) nm; IR (ATR) $\upsilon_{max}$ IR (ATR) $\upsilon_{max}$ 3305, 2918, 2851, 1755, 1718, 1671, 1643, 1576, 1546, 1420, 1327, 1272, 1079, 1033, 718, 668 cm$^{-1}$; $^1$H and $^{13}$C NMR (Table 5); HRESIMS [M+Na]$^+$ m/z 499.3263 (calcd for C$_{26}$H$_{44}$N$_4$O$_4$Na$^+$, 499.3255).

TABLE 1

$^1$H and $^{13}$C NMR data (500 MHz for $^1$H, 125 MHz for $^{13}$C, DMSO-d6)

Biemamide A (1)

| Position | $\delta_C$, mult. | $\delta_H$, (J in Hz) | $^1$H—$^1$H COSY* | HMBC** |
|---|---|---|---|---|
| 1 | 153.3, qC | | | |
| 2 | 169.2, qC | | | |
| 3 | 47.7, CH | 4.55, m | 3-NH, 4 | 2, 4 |
| 4 | 39.0, CH$_2$ | 3.23, m; 3.09, m | 3, 4-NH | 1, 2, 3 |
| 5 | 170.8, qC | | | |
| 6 | 35.3, CH$_2$ | 2.30, dt (2.9, 7.0) | 7 | 5, 7 |
| 7 | 35.1, CH$_2$ | 3.22, m | 6, 7-NH | 6, 8 |
| 8 | 172.2, qC | | | |
| 9 | 35.4, CH$_2$ | 2.02, t (7.1) | 10 | 8, 10, 11 |
| 10 | 25.3, CH$_2$ | 1.45, m | 9, 11 | 8, 9, 11, 12 |
| 11 | 28.7, CH$_2$ | 1.21, m | 10 | 10 |
| 12-18 | 28.9-29.3, CH$_2$ | 1.19-1.27, m | | |
| 19 | 26.8, CH$_2$ | 1.23, m | 20 | 20 |
| 20 | 38.5, CH$_2$ | 1.13, m | 19, 21 | 18, 19, 22, 23 |
| 21 | 27.4, CH | 1.49, m | 20, 22, 23 | 19, 20, 22, 23 |
| 22 | 22.6, CH$_3$ | 0.84, d (6.7) | 21 | 20, 21, 23 |
| 23 | 22.6, CH$_3$ | 0.84, d (6.7) | 21 | 20, 21, 22 |
| 24 | 27.1, CH$_3$ | 2.97, s | | 1, 2 |
| 3-NH | | 8.38, d (7.8) | 3 | 3, 5 |
| 4-NH | | 7.94, d (3.9) | 4 | 1, 3, 4 |
| 7-NH | | 7.80, t (5.6) | 7 | 7, 8 |

TABLE 2

$^1$H and $^{13}$C NMR data (500 MHz for $^1$H, 125 MHz for $^{13}$C, DMSO-d6)

Biemamide B (2)

| Position | $\delta_C$, mult. | $\delta_H$, (J in Hz) | $^1$H—$^1$H COSY* | HMBC** |
|---|---|---|---|---|
| 1 | 153.3, qC | | | |
| 2 | 169.2, qC | | | |
| 3 | 47.7, CH | 4.55, m | 3-NH, 4 | 2, 4 |
| 4 | 39.0, CH$_2$ | 3.23, m; 3.09, m | 3, 4-NH | 1, 2, 3 |
| 5 | 170.8, qC | | | |
| 6 | 35.3, CH$_2$ | 2.30, m | 7 | 5, 7 |
| 7 | 35.1, CH$_2$ | 3.22, m | 6, 7-NH | 6, 8 |
| 8 | 172.2, qC | | | |
| 9 | 35.4, CH$_2$ | 2.02, t (6.8) | 10 | 8, 10, 11 |
| 10 | 25.3, CH$_2$ | 1.45, m | 9, 11 | 8, 9, 11, |
| 11 | 28.7, CH$_2$ | 1.21, m | 10 | |
| 12-20 | 28.7-29.3, CH$_2$ | 1.15-1.32, m | | |
| 21 | 31.3, CH$_2$ | 1.23, m | | 19, 20, 22, 23 |
| 22 | 22.1, CH$_2$ | 1.26, m | 23 | 20, 21, 23 |
| 23 | 14.0, CH$_3$ | 0.85, t (6.6) | 22 | 21, 22 |
| 24 | 27.1, CH$_3$ | 2.97, s | | 1, 2 |
| 3-NH | | 8.39, d (7.8) | 3 | 3, 5 |
| 4-NH | | 7.95, br s | 4 | 1, 3, 4 |
| 7-NH | | 7.88, br s | 7 | 7, 8 |

TABLE 3

$^1$H and $^{13}$C NMR data (500 MHz for $^1$H, 125 MHz for $^{13}$C, DMSO-d6)

Biemamide C (3)

| Position | $\delta_C$, mult. | $\delta_H$, (J in Hz) | $^1$H—$^1$H COSY* | HMBC** |
|---|---|---|---|---|
| 1 | 153.3, qC | | | |
| 2 | 169.2, qC | | | |
| 3 | 47.7, CH | 4.55, m | 3-NH, 4 | 2, 4 |
| 4 | 39.0, CH$_2$ | 3.23, m; 3.09, m | 3, 4-NH | 1, 2, 3 |
| 5 | 170.8, qC | | | |
| 6 | 35.3, CH$_2$ | 2.30, dt (2.8, 7.0) | 7 | 5, 7 |
| 7 | 35.1, CH$_2$ | 3.22, m | 6, 7-NH | 6, 8 |
| 8 | 172.2, qC | | | |
| 9 | 35.4, CH$_2$ | 2.02, t (7.0) | 10 | 8, 10, 11 |
| 10 | 25.3, CH$_2$ | 1.45, m | 9, 11 | 8, 9, 11, |
| 11 | 28.7, CH$_2$ | 1.22, m | 10 | |
| 12-14 | 28.6-29.2, CH$_2$ | 1.17-1.32, m | | |
| 15 | 26.6, CH$_2$ | 1.97, m | 16 | |
| 16 | 129.7, CH | 5.32, m | 15 | 15, 18 |
| 17 | 129.7, CH | 5.32, m | 18 | 15, 18 |
| 18 | 26.6, CH$_2$ | 1.97, m | 17, 19 | 19, 20 |
| 19 | 27.0, CH$_2$ | 1.29, m | 18, 20 | 17, 18, 20 |
| 20 | 38.1, CH$_2$ | 1.14, m | 19, 21 | 19, 22, 23 |
| 21 | 27.3, CH | 1.50, m | 20, 22, 23 | 19, 20, 22, 23 |
| 22 | 22.5, CH$_3$ | 0.84, d (6.6) | 21 | 20, 21, 23 |
| 23 | 22.5, CH$_3$ | 0.84, d (6.6) | 21 | 20, 21, 22 |
| 24 | 27.1, CH$_3$ | 2.97, s | | 1, 2 |
| 3-NH | | 8.40, d (8.0) | 3 | 3, 5 |
| 4-NH | | 7.95, d (4.0) | 4 | 1, 3, 4 |
| 7-NH | | 7.83, d (5.6) | 7 | 7, 8 |

TABLE 4

$^1$H and $^{13}$C NMR data (500 MHz for $^1$H, 125 MHz for $^{13}$C, DMSO-d6)

Biemamide D (4)

| Position | $\delta_C$, mult. | $\delta_H$, (J in Hz) | $^1$H—$^1$H COSY* | HMBC** |
|---|---|---|---|---|
| 1 | 153.3, qC | | | |
| 2 | 169.2, qC | | | |
| 3 | 47.7, CH | 4.55, m | 3-NH, 4 | 2, 4 |
| 4 | 39.0, CH$_2$ | 3.23, m; 3.09, m | 3,4-NH | 1, 2, 3 |
| 5 | 170.8, qC | | | |
| 6 | 35.3, CH$_2$ | 2.30, dt (2.7, 7.0) | 7 | 5, 7 |
| 7 | 35.1, CH$_2$ | 3.22, m | 6, 7-NH | 6, 8 |
| 8 | 172.2, qC | | | |
| 9 | 35.4, CH$_2$ | 2.02, t (7.0) | 10 | 8, 10, 11 |
| 10 | 25.3, CH$_2$ | 1.45, m | 9, 11 | 8, 9, 11 |
| 11 | 28.7, CH$_2$ | 1.23, m | 10 | |
| 12-13 | 28.3-28.7, CH$_2$ | 1.20-1.23, m | | |
| 14 | 29.2, CH$_2$ | 1.29, m | 15 | 13, 16 |
| 15 | 26.6, CH$_2$ | 1.98, m | 14, 16 | 16 |
| 16 | 129.7, CH | 5.32, m | 15 | 15, 18 |
| 17 | 129.7, CH | 5.32, m | 18 | 15, 18 |
| 18 | 26.6, CH$_2$ | 1.98, m | 17, 19 | 17, 19 |
| 19 | 29.2, CH$_2$ | 1.29, m | 18 | 17, 20 |
| 20 | 28.3-28.7, CH$_2$ | 1.20-1.23, m | | |
| 21 | 31.2, CH | 1.24, m | | 22 |
| 22 | 22.1, CH$_3$ | 1.25, m | 21 | 21, 23 |
| 23 | 14.0, CH$_3$ | 0.85, t (6.7) | 21 | 21, 22 |
| 24 | 27.1, CH$_3$ | 2.97, s | | 1, 2 |
| 3-NH | | 8.40, d (8.0) | 3 | 3, 5 |
| 4-NH | | 7.95, d (4.0) | 4 | 1, 3, 4 |
| 7-NH | | 7.83, t (5.7) | 7 | 7, 8 |

TABLE 5

$^1$H and $^{13}$C NMR data (500 MHz for $^1$H, 125 MHz for $^{13}$C, DMSO-d6)

Biemamide E (5)

| Position | $\delta_C$, mult. | $\delta_H$, (J in Hz) | $^1$H—$^1$H COSY* | HMBC** |
|---|---|---|---|---|
| 1 | 153.3, qC | | | |
| 2 | 169.2, qC | | | |
| 3 | 47.7, CH | 4.55, m | 3-NH, 4 | 2, 4 |
| 4 | 39.0, CH$_2$ | 3.23, m; 3.09, m | 3, 4-NH | 1, 2, 3 |
| 5 | 170.8, qC | | | |
| 6 | 35.3, CH$_2$ | 2.30, m | 7 | 5, 7 |
| 7 | 35.2, CH$_2$ | 3.22, m | 6, 7-NH | 6, 8 |
| 8 | 172.2, qC | | | |
| 9 | 35.4, CH$_2$ | 2.01, t (7.1) | 10 | 8, 10, 11 |
| 10 | 25.3, CH$_2$ | 1.45, m | 9, 11 | 8, 9, |
| 11-14 | 28.6-28.8, CH$_2$ | 1.17-1.27, m | | |
| 15 | 26.7, CH$_2$ | 2.00, m | 14, 16 | 14, 16, 17 |
| 16 | 129.8, CH | 5.32, m | 15 | 15, 18 |
| 17 | 127.8, CH | 5.30, m | 18 | 15, 19 |
| 18 | 25.3, CH$_2$ | 2.73, t (6.5) | 17 | 16, 17, 19, 20 |
| 19 | 127.8, CH | 5.30, m | 18 | 17, 21 |
| 20 | 129.8, CH | 5.32, m | 21 | 18, 21, 22 |
| 21 | 26.7, CH$_2$ | 2.00, m | 20, 22 | 19, 20, 22, 23 |
| 22 | 29.1, CH$_2$ | 1.31, m | 21 | 21, 23, 24 |
| 23 | 31.0, CH$_2$ | 1.24, m | | 22, 24, 25 |
| 24 | 22.0, CH$_2$ | 1.26, m | 25 | 23, 25 |
| 25 | 14.0, CH$_3$ | 0.85, t (6.6) | 24 | |
| 26 | 27.1, CH$_3$ | 2.97, s | | 1, 2 |
| 3-NH | | 8.40, d (8.0) | 3 | 3, 5 |
| 4-NH | | 7.95, d (3.4) | 4 | 1, 3, 4 |
| 7-NH | | 7.83, t (5.4) | 7 | 7, 8 |

Figure 1:
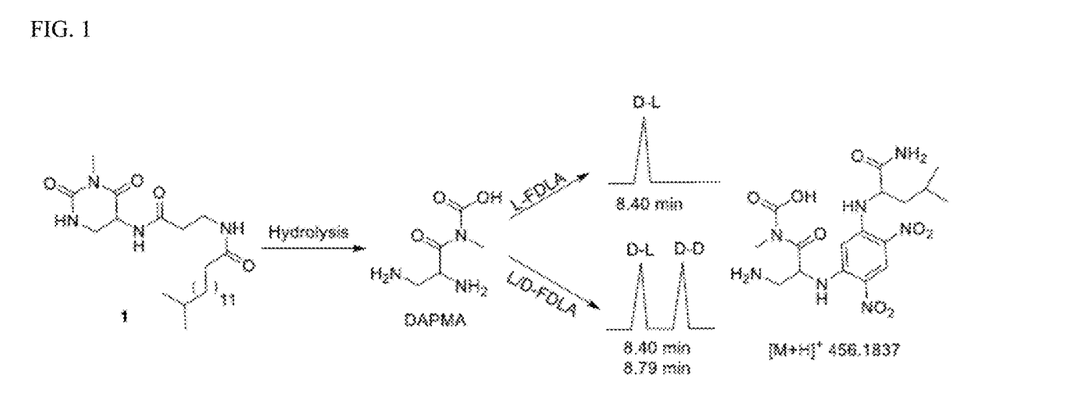
FIG. 1 shows the absolute configuration of compound 1 (biemamide A) by Marfey's advanced method.

Determination of Amino Acid Configurations:

The absolute configurations of Compounds 1 and 2 were elucidated via application of Marfey's advanced method (Marfey, P. Carlsberg Res. Commun. 1984, 49, 591-596). Biemamide A (1) (0.5 mg) was hydrolyzed with 6 N HCl (1 mL) for 14 h at 110° C. and dried under vacuum. The acid hydrolysate was dissolved in 100 μL of H$_2$O and split into two equal portions. Each portion was mixed with 1 N NaHCO$_3$(70 μL), acetone (80 μL), and 70 μL of L- or DL-FDLA (10 mg/mL in acetone). Each solution was stirred for 1 h at 40° C. The reaction was quenched with 1 N HCl (70 μL) and dried under vacuum. A portion of each product was dissolved in CH$_3$OH (1:1) for UHPLC/HRMS analysis. Separation of the derivatives was achieved with a Phenomenex Kinetex C 18 reversed-phase column (2.6 m, 2.1×100 mm) at a flow rate of 0.3 mL/min and with a linear gradient of H$_2$O (containing 0.1% formic acid) and CH$_3$OH (90:10 to 3:97 over 12 min, and held for 2 min at CH$_3$OH/H$_2$O 97:3). The absolute configuration of the amino acid was determined by comparing the retention times of the L- and DL-FDLA derivatives, which were identified by HRMS. Retention times of the DL-FDLA amino acid derivatives were 8.40 and 8.79 min. The retention times of the L-FDLA amino acid derivatives were 8.40 min. LCMS analysis of the L-FDLA and DL-FDLA products supported the assignments of D-(2,3-diaminopropanoyl)methylcarbamic acid (DAPMA) (FIG. 1).

Conformational Analysis and ECD Calculations:

Systematic conformational analysis for compound 6 was performed via the Spartan 14 software package using the MMFF molecular mechanics force field calculation. Conformers occurring within a 10 kcal/mol energy window from the global minimum were chosen for geometry optimization and energy calculation using DFT with the B3LYP functional and the 6-31(d) basis set with the Gaussian09 program. TD-DFT with the basis set B3LYP/6-31G(d) was used to calculate the spin-allowed excitation energies and rotatory (R$_n$) and oscillator strengths (f$_n$) of the lowest 50 excited states. The overall ECD spectra were then generated according to Boltzmann weighting of each conformer. All quantum computations were performed using the Gaussian09 package, performed on a Dell Precision T5500 Linux workstation with a Xeon processor (3.3 GHz, 6-core).

Figure 2:
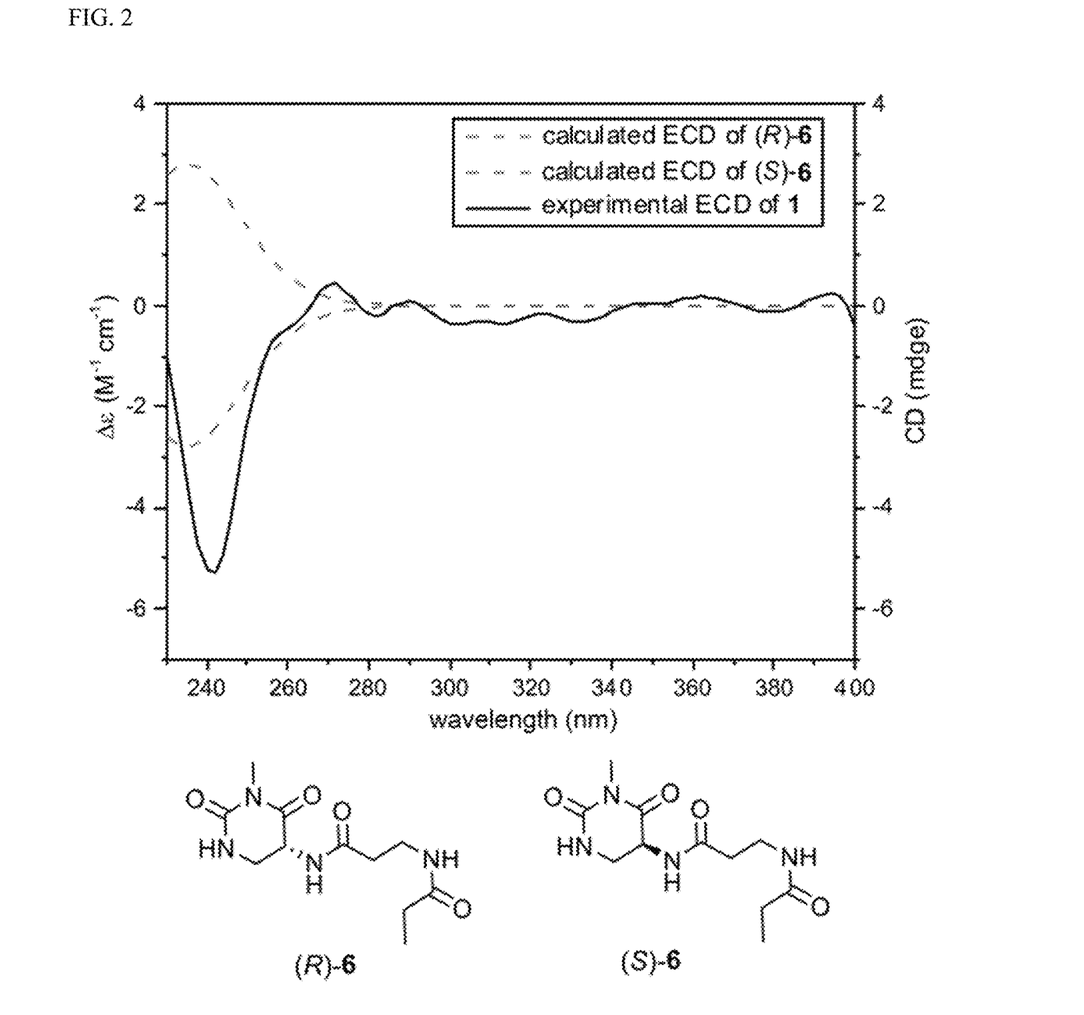
FIG. 2 shows the CD spectrum of compound 1 in CH$_3$OH/CHCl$_3$ (1:1) and calculated ECD spectra of two enantiomers, (3R)-6 and (3S)-6.

The overall calculated ECD spectra of (R)-6 and (S)-6 were generated by Boltzmann distribution of the eight lowest energy conformers with 94.5%, 1.4%, 1.4%, 1.1%, 1.0%, 0.4%, 0.2% and 0.1%. The overall experimental CD spectra of compound 1 compared well only to that of the calculated ECD spectrum of (R)-6; both showed negative Cotton effects (CE) in the regions of 230-260 nm (FIG. 2). Therefore, the absolute configuration of compound 1 was deduced to be 3R.

Aldehyde 7: Compound 3 (150 μg) was dissolved in THF and H$_2$O (1:1 v/v, 1 mL). While stirring, 20 mg of NaIO$_4$ was added to the solution. OsO$_4$ (0.25 mg in t-Butanol) was slowly added to the solution. The solution was stirred at room temperature for 1 h. THF was removed using rotary evaporation, and the remaining aqueous phase was extracted twice with CH$_2$Cl$_2$. The CH$_2$C$_{12}$ portions were dried using rotary evaporation to yield about 100 μg of crude product, containing aldehyde 7. The crude product was analyzed by (−)-ESIMS and (+)-HRESIMS to determine the structure of 7. 7: (−)-ESIMS m/z 367 [M-H]$^-$ and (+)-HRESIMS m/z 391.1935 [M+Na]$^+$ (calcd for C$_{17}$H$_{28}$N$_4$O$_5$Na, 391.1952). In a similar manner, the olefin oxidative cleavage products of 4 and 5 by OsO$_4$—NaIO$_4$ were generated, which had the same MS data as aldehyde 7.

HRMS data indicated that both compounds 3 and 4 possess the molecular formula C$_{24}$H$_{42}$N$_4$O$_4$. Additionally, $^1$H and $^{13}$C NMR data (Tables 3 and 4) for compounds 3 and 4 revealed a high degree of structural similarity to compounds 1 and 2, although both compounds 3 and 4 appeared to contain an olefin within each respective lipid chain. Both olefins were assigned as Z on the basis of $^{13}$C NMR chemical shifts and the realization that allylic carbons of linear olefins of the Z-isomers resonate at higher field than those of E-isomers (Z ~27 ppm; E ~32 ppm). Olefin positions for compounds 3 and 4 were then determined on the basis of HRMS for semi-synthetic oxidatively cleaved variants of compounds 3 and 4. Subjection of both 3 and 4 to NaIO$_4$/OsO$_4$ led, predictably, to aldehyde installation—both reactions afforded 7.[15] HRMS supporting the molecular formula C$_{17}$H$_{28}$N$_4$O$_5$ for 7 along with all other spectral data revealed the Z olefin to reside between C-17 and C-16 of aldehyde precursors 3 and 4.

The elemental composition of compound 5 was established as C$_{26}$H$_{44}$N$_4$O$_4$ on the basis of HRESIMS and NMR data revealed that compound 5 possessed a core scaffold almost identical to that of compound 4. Clear however in spectra of both compounds 4 and 5 was the presence of an additional olefinic signal within the lipid chain of compound 5 relative to compound 4. Analysis of 2D NMR (Table 5), showed the regiochemistry of both olefins within the pendant lipid of compound 5 and this assignment was readily validated by HRMS analyses of semi-synthetically oxidized compound 5. The $^{13}$C NMR chemical shifts of the allylic methylene carbons C-15 ($\delta_C$ 26.7), C-18 ($\delta_C$ 25.3), and C-21 ($\delta_C$ 26.7) suggested that the geometric conformation of the two olefins were Z.

Structural characterization of compounds 1-5 was completed upon assigning stereochemistry to compounds 2-5. Based on the C-3 assignment for compound 1 and the structural/biosynthetic relatedness of all species described herein, compounds 2-5 were assigned as 3R. The absolute configurations for compounds 2-5 were confirmed on the basis of CD spectra and comparisons to data achieved for compound 1.

Example 3: Biological Activity of Biemamides A-E

In vitro Studies:

TGF-β Screening Summary.

A total of 3840 fractions, plated on 12 384-well plates, were assayed in a high throughput screen at 10 μM final concentration. For purposes of concentration calculations we set the average molecular weight of each compound in the library at 500 Da. Each fraction had its different mass, therefore different volumes were used for each well in the screening. Z' for the plates were between 0.53 and 0.45. Initial hits were identified as compounds that inhibited the Bright-Glo signal (see below MLEC assay) by more than 84%. Using this criteria, we identified 48 compounds of interest. The 48 initial hits were then re-screened in a 10 point dose response curve in duplicate. The compounds were assayed for both luciferase inhibition and toxicity using CellTiter-Glo (Promega). Of the 48 compounds identified in the HTS assay, 19 inhibited TGF-β activated luciferase activity without inducing mink lung cell toxicity.

MLEC Luciferase Assay.

MLEC were plated into 384-well plates at a density of 5000 cells/well using Micro-flow (Biotek) multi well reagent dispenser and incubated overnight at 37° C. in the $CO_2$ incubator. 1 μM control SB431542 or 10 μM of compounds 1-5 were added to the wells using the ECHO 550 (Labcyte), then added 10 μL media with 50 μM TGF-β using Micro-flow and incubated for 24 hours at 37° C. 25 μL Bright-Glo (Promega) was added using Micro-flow, and agitated for 4 minutes. The Enspire (Perkin Elmer) plate reader was used to measure the TGF-β response in each well. The luciferase activity was reported as relative light units (RLU), and the readout of each tested fraction was then normalized against negative controls.

Dose-response TGF-β data and cytotoxicity assays using fibroblasts were employed to more rigorously evaluate the 48 initial hits. Three active wells (G8, G9, G10) from the strain WMMA2266 inhibited TGF-β signaling with $IC_{50}$ values of 38.0, 45.7 and 49.5 ng/mL. Chemical analysis of the secondary metabolites in the active wells/extract fractions of WMMA2266 led to the discovery of five pyrimidinedione derivatives, biemamides A-E (1-5). Subsequent application of the MLEC-based TGF-β inhibition assay revealed that purified compounds 1-5 inhibited TGF-β with $IC_{50s}$ of 51.5, 18.7, 51.5, 101.7, and 83.2 nM, respectively, whereas the positive control SB431532 showed an $IC_{50}$ value of 411 nM.

Fibroblast Cytotoxicity:

1000 normal human dermal fibroblasts cells per well are plated in a 384-well plate. The cells are treated with compounds at 0.1-1 μg/mL (final concentration) for 72 hours. Following treatment CellTiterGLO reagent is used to read luminescence to evaluate the toxicity against fibroblast cells. None of the compounds displayed significant cytotoxicity at the highest concentration 1 μg/mL.

TGF-β Induced EMT in NMuMG Cell Line:

Mouse mammary epithelial cell line NMuMG was purchased from American Tissue Culture Collection (ATCC, Manassas, Va.), and NMuMG were cultured as per ATCC recommendations. Imaging assay: Cells were plated in glass bottomed 96 well imaging plates, at a density of 1,000 cells per well, and were allowed to attach overnight. Cells (with exception of 3 control wells) were treated with 50 pm TGF-β. Along with the TGF-β test compounds 1-5 were added in at various doses, and a set of wells was treated with a known TGF-β inhibitor SB431542 at 1 μM.

Figure 3:
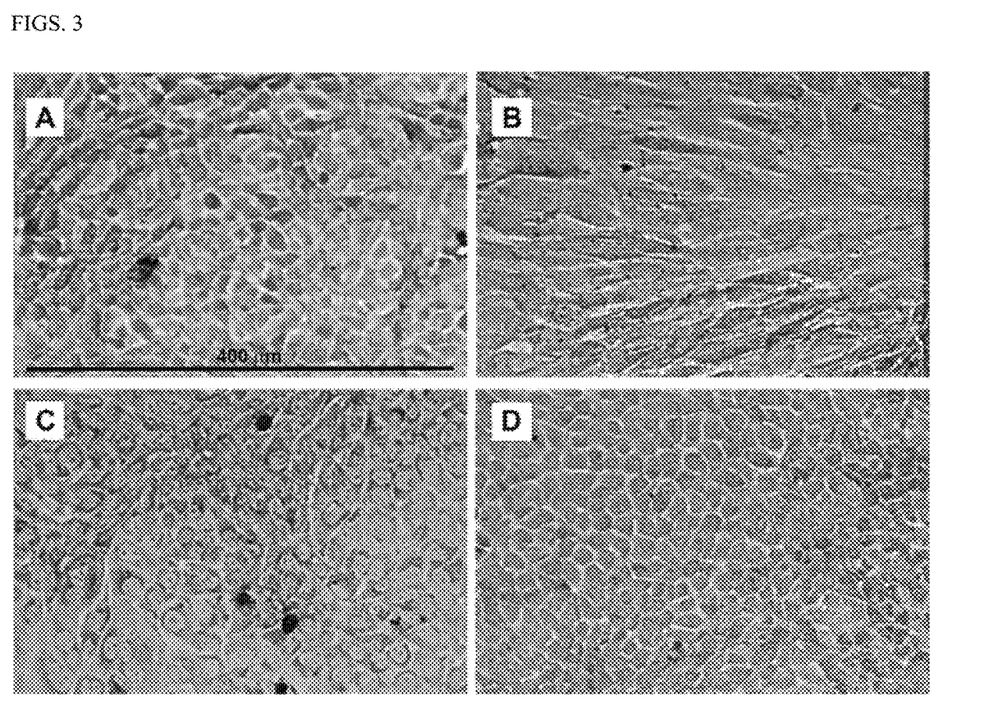
Figure 4:
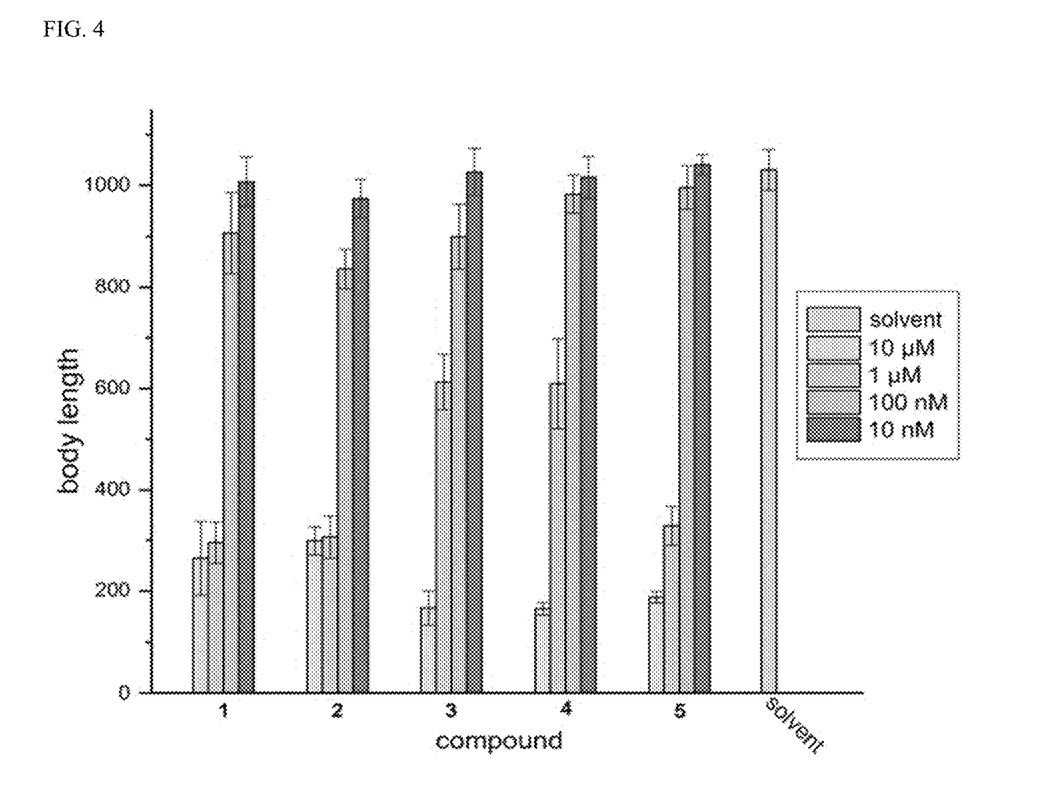
FIG. 4 shows alterations in *C. elegans* development by compounds 1-5.
Figure 5:
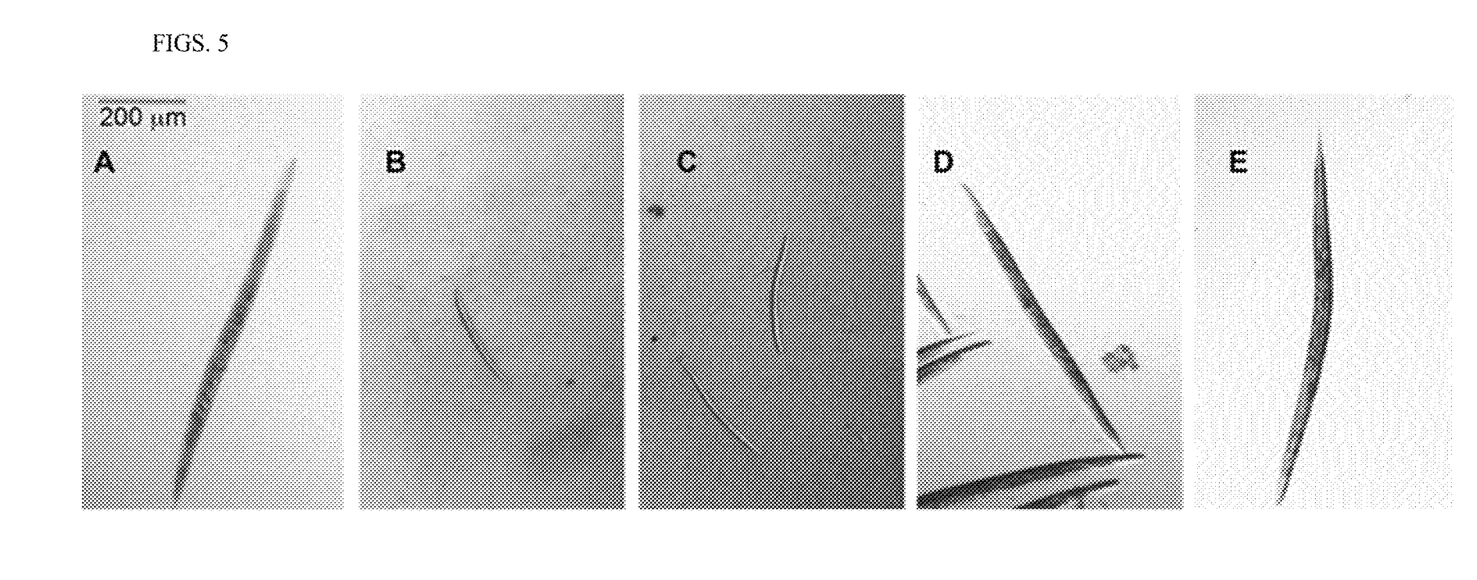

In the absence of TGF-β, NMuMG cells form an epithelial shape; incubation with 50 pM TGF-β for 72 h induces a more fibroblast-like, spindle shaped morphology indicative of mesenchymal cells (FIGS. 3A-3D). As a positive control 1 μM of SB431542 blocked TGF-β-induced transition of the NMuMG epithelial cells into mesenchymal cells. Nine concentrations (160-0.625 nM) of compounds 1-5 were tested for their ability to impact TGF-β signaling in NMuMG cells. The resultant imaging results showed that compounds 1-5 effectively inhibited EMT induction; cells maintained their epithelial phenotype as reflected by data for compound 1 which is shown in FIG. 3C.

An Overview and Description of all 48 Hits from the TGF-β Screening.

In the primary screening, initial hits were identified as compounds that inhibited Bright-Glo (Promega) signal by more than 84%. A total of 3840 fractions from 48 strains were screened at 10 μM, leading to the identification of 48 active fractions. The 48 initial hits were then re-screened in a 10 point dose response curve in duplicate. The compounds were assayed for both luciferase inhibition, and toxicity using CellTiter-Glo. A detailed list of all 48 hits including the mass in each well, the % age of TGF-β inhibition, TGF-β dose-response curves, and cytotoxicity dose-response curves has been generated in a separate spreadsheet (ol-2018-01871m excel). Some of these hits were further evaluated by NMR and LC-MS analyses. For example, hits C04, E04, G03, and G04 from strain WMMA2171 contained staurosporine analogues; staurosporine is a known inhibitor of TGF-β/Smad signaling (Ji, H.; Tang, H.; Lin, H.; Mao, J.; Gao, L.; Liu, J.; Wu, T. Biomed. Rep. 2014, 2, 787-792). Additionally, a number of bafilomycins were observed in hits originating from strain WMMA2244; we did not follow up with bioactivity studies for these species given that they are known structures.

In vivo Studies:

C. elegans Assay.

Synchronized cultures of C. elegans were obtained using the following procedure: a mixed population of worms containing many gravid adults was washed off of two 10 cm NGM plates using distilled water. C. elegans were pelleted at 1000 g in a 15 mL conical tube and the supernatant was discarded. A mix of 3 mL distilled water, 1 mL bleach, and 1 mL 1 M NaOH was added. The tube was inverted for several minutes until it could be observed that the gravid adults had released their eggs. The eggs were pelleted at 1000 g, washed three times with distilled water and suspended in 10 mL of M9 (3.0 g $KH_2PO_4$, 6.0 g $Na_2HPO_4$, 0.5 g NaCl, 1.0 g $NH_4Cl$ into 1 L distilled water). The egg suspension was rotated overnight in a 50 mL conical tube during which the embryos hatched and arrested at the L1 stage. The C. elegans were washed twice and diluted with M9 to reach an approximate concentration of 20 worms/10 μL. Each well in a 96-well plate was prepared by adding 10 μL worm suspension, 0.5 μg OP50 E. coli, 1 μL DMSO (control) or 1 μL DMSO with compounds, and brought to a final volume of 100 μL with M9 plus cholesterol (5 μg/mL). The plates were incubated in a humidified box at 23° C. for 72 hours. To immobilize worms to measure body length the worms were killed by immersing the 96-well plate in a 70° C. water bath for several minutes. Each experiment was performed in triplicate within each plate.

In *C. elegans*, two TGF-β-related pathways regulating dauer formation or body length have been identified, the Dauer pathway and the Sma/Mab pathway (Savage-Dunn, C. TGF-β signaling (Sep. 9, 2005), WormBook, ed. The *C. elegans* Research Community, WormBook, doi/10.1895/wormbook.1.22.1, http://www.wormbook.org.). *C. elegans* use TGF-β related signaling to regulate dauer formation. In addition to the dauer/TGF-β pathway, a second TGF-β related pathway Sma/Mab has been identified in *C. elegans* (Padgett, R. W.; Das, P.; Krishna, S. *Bioessays* 1998, 20, 382-390). Mutations in this pathway are characterized by small body size (Sma) and male tail defects (Mab). These two homologous pathways are genetically distinct, utilizing different ligands, type I receptors, and Smads. Only the type II receptor DAF-4 is shared between the two. Therefore, the compounds of the present technology may inhibit TGF-β signaling through the Dauer or Sma/Mab pathways individually or in tandem.

All *C. elegans* were microscopically imaged, and body length assessments were carried out (FIGS. 4 and 5A-5E). *C. elegans* subjected only to solvent (control) had grown to adulthood, as evidenced by the onset of egg production as well as attainment of a typical adult size. Worms subjected to the highest concentration (10 μM) of compounds 1-5 clearly displayed signs of late development and small body type individuals were easily detected. Unlike the in vitro system, no good TGF-β inhibitory positive controls were available for *C. elegans* studies. However, at reduced biemamide A-E (1-5) concentrations, a dose-dependent effect on development and body size regulation was clearly observed. These in vivo results suggest compounds of the present technology can inhibit TGF-β related pathways with effective concentrations spanning 100 nM and 1 μM and with likely $IC_{50}$ values in the realm of ~300 nM. SB431542, which had been shown to inhibit TGF-β induced EMT in NMuMG cells in vitro, did not alter *C. elegans* size under three concentrations spanning 1 μM→100 μM.

As illustrated in the examples above, the compounds of the present technology are effective TGF-β inhibitors. Importantly, the compounds of the present technology potently suppress TGF-β signaling both in vitro and in vivo, suggesting that neither membrane permeability nor metabolic liabilities should prevent their continued development.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of treatment comprising administering to a mammal suffering from a disease or disorder mediated by TGF-β signaling, an effective amount of a compound of Formula I, a stereoisomer, tautomer, and/or pharmaceutically acceptable salt thereof or a pharmaceutical composition comprising the effective amount of the compound of Formula I, stereoisomer, tautomer, and/or pharmaceutically acceptable salt thereof, and a pharmaceutically acceptable carrier, wherein the compound of Formula I has the structure

(I)

and wherein:
  $R^1$ is a $C_{12}$-$C_{18}$ alkyl or alkenyl;
  $R^2$ is a $C_1$-$C_6$ alkyl; and
  n is 1, 2, 3, 4, 5, or 6.

2. The method of claim 1, wherein the isolated compound is a compound of Formulae IIA, IIB, IIC, IID, or IIE,

(IIA)

(IIB)

(IIC)

(IID)

(IIE)

tautomers thereof and/or pharmaceutically acceptable salts thereof.

3. The method of claim 1, wherein the mammal is human.

4. The method of claim 1, wherein the disease or disorder is liver fibrosis, lung fibrosis, kidney fibrosis, skin fibrosis, or myelofibrosis.

5. The method of claim 1, wherein the disease or disorder is selected from the group consisting of hepatocellular carcinoma or non-small cell lung cancer.

6. A method of inhibiting TGF-β signaling comprising contacting a TGF-β signaling system with an effective amount of a compound of Formula I:

(I)

a stereoisomer, a tautomer, or a pharmaceutically acceptable salt thereof;

wherein:
  $R^1$ is a C12-Cis alkyl or alkenyl;
  $R^2$ is a $C_1$-$C_6$ alkyl; and
  n is 1, 2, 3, 4, 5, or 6;

or a pharmaceutical composition comprising the effective amount of the compound of Formula I, stereoisomer, tautomer, and/or pharmaceutically acceptable salt thereof, and a pharmaceutically acceptable carrier, wherein the effective amount inhibits TGF-β signaling.

7. The method of claim 6, wherein the compound inhibits TGF-β signaling at concentrations of about 0.5 nM to about 100 μM.

8. The method of claim 6, wherein the effective amount inhibits TGF-β induced epithelial mesenchymal transitions (EMT).

9. The method of claim 6, wherein the compound of Formula I is a compound of Formulae IIA, IIB, IIC, IID, or IIE,

(IIA)

(IIB)

(IIC)

(IID)

(IIE)

tautomers thereof and/or pharmaceutically acceptable salts thereof.

* * * * *

UNITED STATES PATENT AND TRADEMARK OFFICE
CERTIFICATE OF CORRECTION

PATENT NO. : 10,889,551 B2
APPLICATION NO. : 16/551534
DATED : January 12, 2021
INVENTOR(S) : Timothy Bugni et al.

Page 1 of 1

It is certified that error appears in the above-identified patent and that said Letters Patent is hereby corrected as shown below:

In the Claims

Column 24, Claim 6, Line 16 should read, "$R^1$ is a $C_{12}$-$C_{18}$ alkyl or alkenyl;"

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*